US006552232B2

(12) United States Patent
Mehnert et al.

(10) Patent No.: US 6,552,232 B2
(45) Date of Patent: Apr. 22, 2003

(54) PROCESS FOR CONDUCTING ALDOL CONDENSATION REACTIONS IN IONIC LIQUID MEDIA

(75) Inventors: Christian Peter Mehnert, Clinton, NJ (US); Nicholas Charles Dispenziere, Wall, NJ (US); Richard Henry Schlosberg, Bridgerwater, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 98 days.

(21) Appl. No.: 09/891,984

(22) Filed: Jun. 26, 2001

(65) Prior Publication Data

US 2003/0050512 A1 Mar. 13, 2003

(51) Int. Cl.[7] .................. C07C 45/72; C07C 45/75; C07C 31/18; C07C 27/16
(52) U.S. Cl. .................. 568/463; 528/853; 528/854
(58) Field of Search ................. 568/463, 853, 568/854

(56) References Cited

U.S. PATENT DOCUMENTS

| 4,156,636 A | 5/1979 | Muller et al. | ................. 204/77 |
|---|---|---|---|
| 5,386,062 A | 1/1995 | Teles et al. | ................. 568/463 |
| 5,731,101 A | * 3/1998 | Sherif et al. | |
| 5,824,832 A | * 10/1998 | Sherif et al. | |
| 5,831,097 A | * 11/1998 | Ebel et al. | |
| 6,090,986 A | * 7/2000 | Godwin et al. | |

FOREIGN PATENT DOCUMENTS

| WO | WO 00/15594 | * 3/2000 |
|---|---|---|
| WO | WO 00/32572 | * 6/2000 |

* cited by examiner

Primary Examiner—Johann Richter
Assistant Examiner—Sikarl A. Witherspan
(74) Attorney, Agent, or Firm—Joseph C. Wang

(57) ABSTRACT

The present invention is related to a method for forming aldol condensation products, comprising reacting at least one aldehyde starting material in the presence of an ionic liquid medium and a basic catalyst at a temperature range of from about −20° C. to about 300° C. and at a pressure range of from about 1 atm to about 1000 atm for a sufficient time to form the aldol condensation products. The invention is also directed to a method for forming aldol condensation products, comprising reacting at least one aldehyde starting material in the presence of a basic ionic liquid medium at the same parameters specified above. The advantage of the instant invention is the increased selectivity and productivity of the resulting aldol condensation products formed in ionic liquid media, along with the ability to recycle the ionic liquid for use in producing additional aldol condensation products.

31 Claims, No Drawings

PROCESS FOR CONDUCTING ALDOL CONDENSATION REACTIONS IN IONIC LIQUID MEDIA

BACKGROUND OF THE INVENTION

1. Field of the Invention

The present invention relates to aldol condensation reactions, and more specifically, to ionic liquid media for carrying out these reactions.

2. Description of the Related Art

Aldol condensation reactions, or aldolization reactions, are known in the art. See U.S. Pat. No. 6,090,986 to Godwin et al., incorporated by reference herein. Currently aldol reactions are carried out in aqueous solutions, which leads to the production of large quantities of wastewater. This wastewater is detrimental to the environment and cannot be treated or recycled for other uses in a cost-effective manner.

Aldol condensation reactions are also typically accompanied by side reactions that significantly reduce the yield of desired products. The result is that the unwanted products of these side reactions must be separated from the desired products and discarded as waste.

Two types of aldol condensation reactions frequently encountered are the self-aldol condensation (Aldol I) and cross-aldol condensation (Aldol II) reactions. In an Aldol I reaction, two molecules of the same aldehyde starting material react to form a reaction product. Alternatively, in an Aldol II reaction, two different aldehyde starting materials react to form a reaction product. In practice, the condensation of two molecules of the same aldehyde (Aldol I) to form an aldol is usually followed immediately by dehydration to form an unsaturated aldehyde with twice the original number of carbon atoms. In a Aldol II reaction, however, the condensation of two molecules of different aldehydes forms an aldol and, upon dehydration, further forms an unsaturated aldehyde having the sum of the carbon atoms of the two different aldehydes. Both Aldol I and Aldol II reactions are well known in the art, as are the conditions required to effect their condensation.

An important example of Aldol I is the condensation of n-butyraldehyde to form, following a hydrogenation step, 2-ethyl-hexanol, known in the art as a Guerbet alcohol.

U.S. Pat. No. 6,090,986 to Godwin et al. discloses an important example of Aldol II in the formation of 2,4-dimethyl-2-heptenal from condensing 2-methyl-pentanal and propanal. Following the aldol condensation step, the 2,4-dimethyl-2-heptenal product is preferably hydrogenated to produce the saturated aldehyde 2,4-dimethyl-heptanal, which can be further hydrogenated to form the alcohol 2,4-dimethyl heptanol or, alternatively, can be oxidized to form 2,4-dimethyl heptanoic acid. The final alcohol and acid products are in demand commercially.

The Aldol II reaction is often run by reacting formaldehyde and a second aldehyde starting material in a basic catalyst through several steps, including several aldol addition steps and a final crossed Cannizzaro reaction step, to form a neopolyol product. By definition, neopolyols are alcohols having two or more primary alcohol functional groups ($CH_2OH$) plus a tetra-substituted carbon atom. The most commercially desired neopolyol products are pentaerythritol, trimethylol ethane, trimethylol propane, and neopentyl glycol, which are derived from reacting formaldehyde with the second aldehyde starting materials acetaldehyde, propionaldehyde, n-butyraldehyde and isobutyraldehyde, respectively. The formation of neopolyols is disclosed in more detail in *Encyclopedia of Chemical Technology*, Kirk-Othmer, Fourth Edition, Vol. 1, pp. 913–925 (John Wiley & Sons 1991), incorporated by reference herein. The structural formulae for the preferred

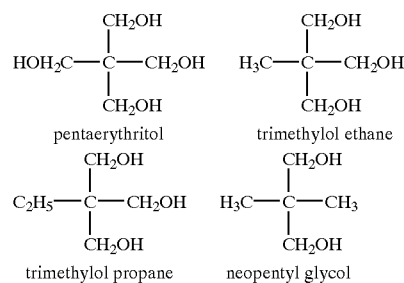

neopolyols are as follows:

Unfortunately, each type of aldol condensation reaction results in the formation of unwanted side products. Hence, there is a need in the art for a method to increase the yield of desired aldol condensation products, while decreasing the amount of side reactions, in an efficient and cost-effective manner. There is also a need for a method to reduce the amount of wastewater produced from present aldehyde condensation reactions.

Ionic liquids are known in the art for use as solvents in various chemical reactions. See U.S. Pat. Nos. 5,824,832 and 5,731,101 both to Sherif et al., and PCT International Patent Publication Nos. WO 00/15594 and WO 00/32572, all incorporated herein by reference. An ionic liquid is a liquid that is composed entirely of ions. They are typically molten at low temperatures and are suitable for use as a catalyst and as a solvent in alkylation and polymerization reactions, as well as in dimerization, oligomerization, acetylation, metatheses, hydrogenation, hydroformylation, and copolymerization reactions.

A class of ionic liquids which is of special interest is the class of salt compositions which are salts with melting points below 100° C. Such compositions are mixtures of components which are liquid at temperatures below the individual melting points of the components.

The application of ionic liquids to aldol condensation reactions has heretofore not been disclosed in the art. One reason is because not all ionic liquids will produce advantageous results when used as the reaction medium or catalyst for such reactions.

SUMMARY OF THE INVENTION

The present invention relates to a process for forming aldol condensation products which comprises reacting at least one aldehyde starting material in the presence of a neutral ionic liquid medium, which is stable towards air and water, and a basic catalyst. In a preferred embodiment, the ionic liquid is comprised of an imidazolium- or pyridinium-based cation and a $BF_4^-$ or $PF_6^-$ anion. The preferred aldehyde starting materials are typically formaldehyde, acetaldehyde, propionaldehyde, n-butyraldehyde and isobutyraldehyde, and mixtures of formaldehyde and one of the foregoing, although other aldehydes are also suitable. The use of an ionic liquid can provide for more convenient separation of the aldol product and/or recycling of the neutral ionic liquid medium.

In another embodiment, the instant invention comprises reacting at least one aldehyde starting material in the presence of a basic ionic liquid medium to form aldol condensation products. The preferred embodiment, in this case, is an ionic liquid that is rendered intrinsically basic by the presence of a hydroxyl group as an anionic species.

In a further embodiment, the present invention relates to a process for producing cross-aldol condensation products by reacting formaldehyde and a second aldehyde starting material in the presence of a neutral ionic liquid medium and basic catalyst. The condensation products are optionally, but preferably, further reacted to form neopolyol products. The preferred second aldehyde starting materials in this situation are acetaldehyde, propionaldehyde, n-butyraldehyde and isobutyraldehyde, while the resulting neopolyol products derived therefrom are pentaerythritol, trimethylol ethane, trimethylol propane, and neopentyl glycol, respectively.

In a similar vein, the just-described formation of neopolyol products may be accomplished by reacting formaldehyde with a second aldehyde starting material in a basic ionic liquid medium to produce the same condensation products and the eventual neopolyol products.

DETAILED DESCRIPTION OF THE INVENTION

The phrase "aldol condensation" or "aldolization" is used herein to refer to the process whereby at least 2 aldehyde starting materials are reacted and, upon immediate dehydration, form aldol condensation products. Aldol I and Aldol II are the terms used to label two types of aldol condensation.

The term "base" or "basic" when used with "catalyst" or "ionic liquid" refers to Brønsted bases having the ability to react with (neutralize) acids to form salts. The pH range of bases is from 7.1 to 14.

The word "neutral" refers to compounds having a pH of 7 under the Brønsted acid-base theory.

The term "neutral ionic liquid" refers to ionic liquids with a molar fraction of (x=0.5) and exhibits neither Brøonsted nor Lewis acidity. This definition is derived from the fact that Lewis acidity can be expressed by the molar fraction (x). Conventionally, when (x=0.5) the mixture is labeled neutral, when (x>0.5) the mixture is labeled acidic, and when (x<0.5) the mixture is labeled basic. For a more detailed explanation of the definition of neutral ionic liquids, see PCT International Patent Publication No. WO 00/15594.

The term "catalyst" is used herein to include all forms of catalysis, including classic initiators, co-initiators, co-catalysts, activating techniques, etc.

The term "neopolyol" refers to an alcohol having two or more primary alcohol functional groups ($CH_2OH$) plus a tetra-substituted carbon atom.

The present invention describes a new method to carry out aldol condensation reactions. By utilizing ionic liquids as reaction medium and/or catalyst it is possible to achieve higher selectivity for aldol condensation products. The investigated ionic systems are salts that have melting points below 100° C. and can be utilized as liquid solvent media or catalysts for a wide variety of chemical processes. Unlike conventional solvent systems, these liquids exhibit low vapor pressure, tunable polarity, and high thermal stability. Depending on the choice of the ionic fragments, a reaction environment can be designed to accommodate the catalysis and the separation of a chemical process in the most efficient way. By combining base catalysis with the advantages of ionic liquids, it is possible to prepare aldol condensation catalyst media which exhibit the significant advantages of selectivity and recyclability over existing catalyst systems.

The ionic liquids used in this invention may be characterized by the general formula $A^+B^-$, where $A^+$ is a cationic species and $B^-$ is an anionic species. The preferred ionic liquid has organic cationic species and inorganic anionic species. The composition $A^+B^-$ may be referred to herein as an ionic liquid moiety.

In one embodiment, this invention utilizes a neutral ionic liquid and a basic catalyst to form aldol condensation products. Preferred basic catalysts are the alkali metal hydroxides and alkali earth metal hydroxides. Most preferably, the basic catalyst is either sodium hydroxide or potassium hydroxide.

While the preparation of the neutral ionic liquids disclosed herein are accomplished using methods known to one skilled the art (see, e.g., U.S. Pat. No. 5,731,101, incorporated by reference herein, and PCT International Patent Publication No. WO 95/21871), a brief summary of their precursor cationic and anionic species follows. Many unsubstituted or substituted heterocyclic ring systems may be converted into a stable cation $A^+$ through the process of alkylation, protonation, acylation or another method known to those skilled in the art (see, e.g., T. L. Gilchrist, "Heterocyclic Chemistry" (Wiley & Sons 1995)). Thus, precursors for $A^+$ may be selected from, for example, imidazoles, pyridines, pyrazoles, thiazoles, isothiazoles, azathiozoles, oxothiazoles, oxazines, oxazolines, oxazoboroles, dithiozoles, triazoles, selenozoles, oxaphospholes, pyrroles, boroles, furans, thiophenes, phospholes, pentazoles, indoles, indolines, oxazoles, isooxazoles, isotriazoles, tetrazoles, benzofurans, dibenzofurans, benzothiophenes, dibenzothiophenes, thiadiazoles, pyrimidines, pyrazines, pyridazines, piperazines, piperidines, morpholenes, pyrans, annolines, phthalzines, quinazolines, quinoxalines, quinolines, isoquinolines, thazines, oxazines, and azaannulenes. In addition, acyclic organic systems are also suitable. Examples include, but are not limited to, amines (including amidines, imines, and guanidines), phosphines (including phosphinimines), arsines, stibines, ethers, thioethers, selenoethers and mixtures of the above.

From the above list, the preferred cationic species of the neutral ionic liquid used herein are either pyridinium- or imidazolium-based. The most preferred cationic species are 1-butyl-3-methyl imidazolium, 1-butyl-2,3-dimethyl imidazolium and 1-butyl-pyridinium. The chemical structures for the three preferred cationic species are drawn as follows:

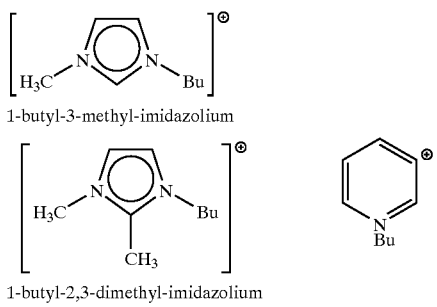

1-butyl-3-methyl-imidazolium 1-butyl-2,3-dimethyl-imidazolium

The precursors for the anionic species B⁻ include, for example, salts, alkylates and halogenated salts of the Group IB, IIIA, IVA, VA, VIA, and VIIA elements of the periodic table, including borates, phosphates, nitrates, sulfates, triflates, halogenated copperates, antimonates, phosphates, phosphites, substituted and unsubstituted carboranes, polyoxo metallates, substituted (fluorinated, alkylated, and arylated) and unsubstituted metalloboranes, substituted and unsubstituted carboxylates and triflates, and mixtures thereof. The periodic table used herein to reference the above-identified groups of elements is from *Hawley's Condensed Chemical Dictionary*, Thirteenth Edition, Richard J. Lewis, Sr., inside front cover (John Wiley & Sons, Inc. 1997). The anion B⁻ may also be a non-coordinating anion such as tetra[pentafluoro phenyl] borane. Examples of some of the above include $BF_4^-$, $PF_6^-$, $CF_3SO_3^-$, $CF_3COO^-$, $SbF_6^-$, $[CuCl_2]^-$, $AsF_6^-$, $SO_4^-$, $CF_3CH_2CH_2COO^-$, $(CF_3SO_2)_3C^-$, $CF_3(CF_2)_3SO_3^-$, $[CF_3SO_2]_2N^-$, or a metal inorganic anion. Most preferably, the anionic species B⁻ will be selected from $BF_4^-$ and $PF_6^-$.

In another embodiment, a basic ionic liquid is used as both the reaction medium and catalyst for producing aldol condensation products. The cationic species A⁺ of the basic ionic liquid is selected from those enumerated above for the cationic species of the neutral ionic liquids. However, the anionic species B⁻ of the basic ionic liquid is a hydroxyl group. This basic ionic liquid is typically formed by reacting an ionic liquid precursor with either an alkali metal hydroxide or alkali earth metal hydroxide in a tetrahydrofuran medium with the loss of a salt, as is known by one skilled in the art. The most preferred anionic species are those prepared from potassium hydroxide or sodium hydroxide. For instance, an imidazolium chloride may be reacted with potassium hydroxide to form the basic ionic liquid imidazolium hydroxide with the loss of a potassium chloride salt. An example of the formation of a basic ionic liquid is shown in Examples 7 and 8 herein.

Any aldehyde may be used as the aldehyde starting material in the present case. The only limitation is that in an Aldol I reaction, two molecules of the same aldehyde starting material react to form aldol condensation products. Alternatively, an Aldol II reaction involves reacting two different aldehyde starting materials to produce the condensation products. The preferred aldehyde starting materials utilized in forming the aldol condensation products are one or more aldehydes having the formula RCHO, wherein R is a hydrogen atom or a straight-chain, branched or cyclic aliphatic group having from 1 to 10 carbon atoms, preferably from 1 to 6 carbon atoms, and most preferably from 1 to 4 carbon atoms.

In a further embodiment, a commercially important application of cross-aldol condensation (Aldol II) is the reaction of formaldehyde with a second aldehyde starting to form a neopolyol. In practice, several intermediate aldol addition steps involving formaldehyde and a final crossed Cannizzaro step take place before producing the neopolyol product. The most preferred second aldehyde starting materials are acetaldehyde, propionaldehyde, n-butyraldehyde and isobutyraldehyde, which, when reacted with formaldehyde, produce the respective neopolyol products pentaerythritol, trimethylol ethane, trimethylol propane and neopentyl glycol.

The above-referenced reactions for forming aldol condensation products may be generally carried out at a pressure of from about 1 atm (atmospheric pressure) to about 1000 atm (elevated pressure). The reaction can be carried out over a wide range of temperatures and is not particularly limited. Usually the reaction temperature is within the range of from about −20° C. to 300° C., more typically within the range of from 50° C. to 250° C., such as from 60° C. to 150° C. Preferably, the temperature ranges from 70° C. to 100° C. Most preferably, the temperature is from 80° C. to 90° C.

The aldol condensation reactions of the instant case may run for approximately from about 1 to 10 hours, preferably from about 2 to 5 hours, and most preferably for about 3 hours.

In the present invention, the ionic liquid phase can be recycled by way of methods known in the art and applied as reaction medium to form additional aldol condensation products. The ionic liquid medium may also be recycled for use in other reactions.

The following non-limiting examples are provided in order to further demonstrate the various embodiments and advantages of some forms of the present invention.

EXAMPLE 1

A self-aldol condensation reaction (Aldol I) of propanal in a sodium hydroxide/water system to form 2-methyl-2-pentenal was run to show the productivity and selectivity results in a conventional non-ionic liquid system. A water solution of sodium hydroxide (1 M) (8.8 mmol, 0.352 g) and decane (internal standard) (5.6 mmol, 0.801 g) was heated to 80° C. to form the reaction medium. Over a period of 5 minutes, propanal (232 mmol, 13.5 g) was added to the stirring mixture. After the addition, the reaction mixture was refluxed for an additional 3 hours at 80° C. The resulting solution turned a light yellow color and was further investigated using gas chromatography (GC) and gas chromatography/mass spectroscopy (GC/MS) techniques. Catalyst evaluation results for Example 1 are presented in the bottom row of Table 1 (shown below).

Table 1 shows that under the reaction conditions specified in columns 2–3 thereof, the Aldol I reaction with propanal as the starting material in a sodium hydroxide/water system (bottom row of Table 1) will yield the desired reaction product 2-methyl-2-pentenal at 81.7 wt % plus other undesired reaction products, such as products with 6 carbon atoms at 0.3 wt % and those with 9 or more carbon atoms at 18.0 wt %.

TABLE 1

Aldol reaction of propanal to 2-methyl-2-pentenal
using imidazolium-based ionic liquids as solvent medium
and sodium hydroxide as catalyst.

| Reaction Medium | Time (min) | Temperature (° C.) | Conversion (wt %) | C6 = (wt %)* | C6 (others) (wt %)* | C9 + higher (wt %)* |
|---|---|---|---|---|---|---|
| [bmin]$BF_4$ | 180 | 80 | 99 | 65.3 | 1.4 | 33.2 |
| [bmin]$PF_6$ | 180 | 80 | 99 | 74.3 | 0.4 | 25.3 |
| [bdmin]$BF_4$ | 180 | 80 | 99 | 67.9 | 0.9 | 30.7 |
| [bdmin]$PF_6$ | 180 | 80 | 100 | 82.1 | 1.0 | 16.8 |
| $H_2O$ | 180 | 80 | 100 | 81.7 | 0.3 | 18.0 |

(Abbreviations: C6 = 2-methyl-2-pentenal; *Selectivity).

EXAMPLE 2

Rows 2–5 of Table 1 exhibit the comparative results of the self-aldol condensation reaction (Aldol I) of propanal in a neutral ionic liquid medium and sodium hydroxide catalyst to produce 2-methyl-2-pentenal. In row 2, the neutral ionic liquid phase 1-butyl-3-methyl imidazolium tetrafluoroborate ([bmin]$BF_4$) (39.1 mmol, 8.9 g) was treated with a water solution (1 ml) of sodium hydroxide (8.8 mmol, 0.352 g) as the basic catalyst and decane (internal standard) (5.6 mmol, 0.72 g). After the resulting mixture was heated to 80° C., propanal (232.4 mmol, 13.5 g) was added. The reaction mixture was kept under reflux condition at 77° C. for 3 hours. After the conclusion of the reaction, the pale yellow mixture was further investigated by GC and GC/MS techniques. The separation of the reaction product 2-methyl-2-pentenal from the ionic liquid phase was carried out via vacuum distillation techniques.

Rows 3–5 of Table 1 show the investigation of the Aldol I reaction carried out in the same basic catalyst as in row 2, but with the following neutral ionic liquid media: 1-butyl-3-methyl imidazolium hexafluorophosphate ([bmin]$PF_6$), 1-butyl-2,3-dimethyl imidazolium tetrafluoroborate ([bdmin]$BF_4$), and 1-butyl-2,3-dimethyl imidazolium hexafluorophosphate ([bdmin]$PF_6$). As shown in row 4 of Table 1, when the Aldol I reaction was carried out in the [bdmin]$PF_6$ ionic liquid phase, the desired reaction product 2-methyl-2-pentenal was produced in a greater amount (82.1 wt %) than in the sodium hydroxide/water medium (81.7 wt %), while resulting in a lower amount of the undesired C9+ higher products (16.8 wt % versus 18.0 wt % for the sodium hydroxide/water medium). All investigations in ionic liquid media have been carried out under identical reaction conditions.

Another advantage of the instant invention is that one skilled in the art can choose different reaction products as the desired product—i.e., increased selectivity. For instance, if one desires to make more C9+ higher reaction products from an Aldol I reaction with propanal, it would be advantageous to use [bmin]$BF_4$ as the ionic liquid medium with sodium hydroxide catalyst because 33.2 wt % of the C9+ higher product would be produced in comparison to only 18.0 wt % for the sodium hydroxide/water medium.

EXAMPLE 3

In a similar manner as Example 1, this example is a cross-aldol condensation reaction (Aldol II) of propanal and 2-methyl-pentanal in a sodium hydroxide/water medium to form the 2,4-dimethyl-2-heptenal product that shows the productivity and selectivity results in a conventional system. The 2-methyl-pentanal starting material (175 mmol, 17.5 g) and nonane (internal standard) (8.7 mmol, 1.12 g) were added to a water solution of sodium hydroxide (1 M) (8.8 mmol, 0.352 g). The resulting mixture was heated to 90° C. and treated with propanal starting material (44.8 mmol, 2.6 g). After the addition, the reaction mixture was refluxed for an additional 3 hours at 90° C. The resulting solution turned a light yellow color and was further investigated using GC and GC/MS techniques. Catalyst evaluation results are presented in the bottom row of Table 2.

TABLE 2

Cross-aldol reaction of propanal and 2-methyl-pentanal to 2,4-dimethyl-2-heptenal using imidazolium-based ionic liquids as solvent medium and sodium hydroxide as catalyst.

| Reaction Medium | Time (min) | Temp. (° C.) | Conversion (wt %) | C6 = (wt %)* | C6 (others) (wt %)* | C9 = (wt %)* | C9 + higher (wt %)* |
|---|---|---|---|---|---|---|---|
| [bmin]$BF_4$ | 180 | 95 | 100 | 4.0 | 2.5 | 79.8 | 13.6 |
| [bmin]$PF_6$ | 180 | 96 | 99.6 | 13.0 | 13.4 | 59.0 | 14.6 |
| [bdmin]$BF_4$ | 180 | 95 | 96.1 | 14.6 | 8.9 | 53.5 | 22.8 |
| [bdmin]$PF_6$ | 180 | 95 | 99.7 | 10.6 | 20.1 | 45.1 | 24.1 |
| $H_2O$ | 180 | 90 | 100 | 35.5 | 0.1 | 59.5 | 4.7 |

(Abbreviations: C6 = 2-methyl-2-pentenal; C9 = 2,4-dimethyl-2-heptenal; *Selectivity).

EXAMPLE 4

Rows 2–5 of Table 2 show the comparative results of the cross-aldol condensation reaction (Aldol II) of propanal and 2-methyl-pentanal starting materials in a neutral ionic liquid medium and sodium hydroxide catalyst. All investigations in ionic liquid media have been carried out under identical reaction conditions. The ionic liquid phase 1-butyl-3-methyl imidazolium tetrafluoroborate ([bmin]$BF_4$) (40.0 mmol, 9.0 g) was treated with a water solution (1 ml) of sodium hydroxide (8.8 mmol, 0.352 g), 2-methyl-pentanal (180 mmol, 18.0 g) and nonane (internal standard) (7.8 mmol, 1.00 g). After the resulting mixture was heated to 90° C., propanal (44.8 mmol, 2.6 g) was added. The reaction mixture was kept under reflux condition at 95° C. for 3 hours. After the conclusion of the reaction, the pale yellow mixture was further investigated by GC and GC/MS techniques. The separation of the products from the ionic liquid phases was carried out via vacuum distillation techniques. Further ionic liquid phases investigated for this Aldol II reaction are 1-butyl-3-methyl imidazolium hexafluorophosphate ([bmin] $PF_6$), 1-butyl-2,3-dimethyl imidazolium tetrafluoroborate ([bdmin]$BF_4$), and 1-butyl-2,3-dimethyl imidazolium hexafluorophosphate ([bdmin]$PF_6$). Catalyst evaluation results are presented in Table 2.

Table 2 is similar to Table 1 but with more columns to reflect the formation of additional aldol condensation products. When the desired reaction product is 2,4-dimethyl-2-heptenal, the [bmin]$BF_4$ ionic liquid produced substantially higher yield (79.8 wt %) than the conventional sodium hydroxide/water medium (59.5 wt %). This shows the clear advantage of using the [bmin]$BF_4$ neutral ionic liquid medium with sodium hydroxide catalyst for the cross-aldol condensation reaction of propanal and 2-methyl-pentanal.

In the cross-aldol condensation reaction (Aldol II), it is very important that both substrates have high enough concentrations in the reaction phase. In the sodium hydroxide/water system, the substrate propanal is fully water-soluble while the other substrate 2-methyl-pentanal exhibits only limited solubility. Although the reaction is already carried out with a four-fold excess of 2-methyl-pentanal to compensate for the low solubility, the reaction only reaches a product selectivity of 59.5% (row 6, column 7 of Table 2). The major side reaction occurs through the self-condensation of propanal to form 2-methyl-2-pentenal with a selectivity of 35.5% (row 6, column 5 of Table 2). By carrying out the same reaction under identical conditions in the basic ionic liquid phase [bmin]$BF_4$, the side reaction was reduced to only 4% (row 2, column 5 of Table 2) and the product selectivity for 2,4-dimethyl-2-heptenal increased to 79.8% (row 2, column 7 of Table 2). While not wishing to be bound by any theory, the significant improvements of the selectivity are contributed to the higher solubility of the substrate 2-methyl-pentanal in the ionic liquid phase. The polarities of the ionic liquid phases can be adjusted through structural variations, and further improvements of the selectivity should be possible through fine-tuning of the ionic liquid polarities.

EXAMPLE 5

A self-aldol condensation reaction (Aldol I) of propanal starting material in the basic ionic liquid medium 1-butyl-2,3-dimethyl imidazolium hydroxide was run to produce 2-methyl-2-pentenal. The basic ionic liquid 1-butyl-2,3-dimethyl imidazolium hydroxide (8.8 mmol, 1.51 g) and decane (5.3 mmol, 0.76 g) were heated to 80° C. After the addition of propanal (232 mmol, 13.5 g) the reaction mixture was refluxed at 80° C. for 3 hours. The resulting products were analyzed using GC and GC/MS techniques. The product isolation was carried out by vacuum distillation. Catalyst evaluation results are presented in Table 3 (below). While the desired product 2-methyl-2-pentenal produced at 38.3 wt % is lower than those shown in Table 1, the selectivity of the various reaction products is different. This difference in selectivity allows one the flexibility to choose which reaction products to form. For instance, the formation of 3-hydroxy-2-methyl-pentanal at 37.5 wt % can be considered commercially advantageous and could not be produced using the conventional sodium hydroxide/water system.

TABLE 3

Aldol reaction of propanal to 2-methyl-2-pentenal using 1-butyl-2,3-dimethyl imidazolium hydroxide as catalyst and reaction medium:

| Time (min) | Temperature (° C.) | Conversion (%) | $C6^-$ (%) | $C6^{(3-OH)}$ (%) | C6 (others) (%) | C9 + higher (%) |
|---|---|---|---|---|---|---|
| 180 | 80 | 81 | 38.3 | 37.5 | 0.6 | 23.7 |

(Abbreviations: $C6^-$ 2-methyl-2-pentenal; $C6^{(3-OH)}$ 3-hydroxy-2-methyl-pentanal)

EXAMPLE 6

A cross-aldol condensation reaction of propanal and 2-methyl-pentanal in the basic ionic liquid medium 1-butyl-2,3-dimethyl imidazolium hydroxide was run to form 2,4-dimethyl-2-heptenal. The basic ionic liquid 1-butyl-2,3-dimethyl imidazolium hydroxide (8.7 mmol, 1.50 g), 2-methyl-pentanal (1 79.7 mmol, 18.0 g), and nonane (7.8 mmol, 1.01 g) were heated to 100° C. After the addition of propanal (44.7 mmol, 2.6 g), the reaction mixture was refluxed at 87° C. for 3 hours. The resulting products were analyzed using GC and GC/MS techniques. The product isolation was carried out by vacuum distillation. Catalyst evaluation results are presented in Table 4.

TABLE 4

Cross-aldol reaction of propanal and 2-methyl-pentanal to 2,4-dimethyl-2-heptenal using 1-butyl-2,3-dimethyl imidazolium hydroxide as catalyst and reaction medium:

| Time (min) | Temperature (° C.) | Conversion (%) | $C6^-$ (%) | C6 (others) (%) | $C9^-$ (%) | C9 (others) + Higher (%) |
|---|---|---|---|---|---|---|
| 120 | 99 | 82 | 34.8 | 5.9 | 34.7 | 24.3 |

(Abbreviations: $C6^-$ 2-methyl-2-pentenal; $C9^-$ 2,4-dimethyl-2-heptenal).

EXAMPLE 7

To prepare a basic ionic liquid phase that is both a catalyst and a solvent medium, it was first necessary to prepare the ionic liquid precursor. Example 7 shows the production of the precursor 1-butyl-2,3-dimethyl imidazolium chloride, while Example 8 displays the formation of the basic ionic liquid 1-butyl-2,3-dimethyl imidazolium hydroxide.

For the preparation of the 1-butyl-2,3-dimethyl imidazolium chloride ([bdmin]Cl) ionic liquid precursor, 1-chlorobutane (408.2 g, 4.4 mol) was added to 1,2-dimethyl imidazole (141.3 g, 1.5 mol) which had been liquefied in a four neck round bottom flask equipped with a reflux condenser, nitrogen purge, thermometer/thermowatch and an air stirrer. The clear, pale yellow solution was heated overnight with stirring at reflux (85° C.). The viscosity of the solution increased and a white-colored solid started to form. The heating was continued for two additional days, while monitoring the product formation using $^1H$ and $^{13}C$ NMR spectroscopy (following the conversion of the 1,2-dimethyl imidazole substrate). The resulting material was a viscous oil containing white and tan colored solids. After evaporation of the volatiles under reduced pressure ($10^{-2}$ torr), the tan colored solid was washed with anhydrous diethyl ether and filtered through a Buchner funnel. The resulting material was dried under reduced pressure ($10^{-2}$ torr) giving the white colored complex 1-butyl-2,3-dimethyl imidazolium chloride (226.3 g, 1.2 mol) in 80% yield. $^1$H-NMR (CDCl$_3$): 0.95 (m, 3H, CH$_2$—C$\underline{H}_3$), 1.39 (m, 2H, C$\underline{H}_2$—CH$_3$), 1.82 (m, 2H, C$\underline{H}_2$—CH$_2$—C$\underline{H}_3$), 2.87 (s, 3H, C2I—C$\underline{H}_3$), 4.08 (s, 3H, N1—C$\underline{H}_3$), 4.31 (m, 2H, N$_3$—C$\underline{H}_2$), 7.78 (s, 1H, C5I-$\underline{H}$), 7.95 (s, 1H, C4I-$\underline{H}$). $^{13}$C—NMR (CDCl$_3$): 9.2 (CH$_2$—$\underline{C}$H$_3$), 12.2 ($\underline{C}$H$_2$—CH$_3$), 18.1 ($\underline{C}$H$_2$—CH$_2$—CH$_3$), 30.5 (C2I—$\underline{C}$H$_3$), 34.5 (N1—$\underline{C}$H$_3$), 47.2 (N3—$\underline{C}$H$_2$), 129.2 ($\underline{C}$4I), 121.8 ($\underline{C}$5I), 142.1 ($\underline{C}$2I).

EXAMPLE 8

In preparing the basic ionic liquid 1-butyl-2,3-dimethyl imidazolium hydroxide ([bdmin]OH), the precursor complex 1-butyl-2,3-dimethyl imidazolium chloride (0.1 mol, 18.9 g) and a fine powder of potassium hydroxide (0.1 mol, 5.6 g) were combined and treated with tetrahydrofuran (25 ml) giving a tan-colored slurry. After stirring the mixture at room temperature for 12 hours, the material turned dark brown. The resulting material was filtered and the volatiles removed under reduced pressure ($10^{-2}$ torr). The viscous product was treated with tetrahydrofuran (30 ml), which resulted in the formation of a precipitate. After filtration and evaporation of the volatiles, the ionic liquid phase was dried under reduced pressure ($10^{-2}$ torr) giving a dark brown liquid. $^1$H-NMR (d$^6$-toluene/TMS): 0.86 (m, 3H, CH$_2$—C$\underline{H}_3$), 1.28 (m, 2H, C$\underline{H}_2$—CH$_3$), 1.47 (m, 2H, C$\underline{H}_2$—CH$_2$—CH$_3$), 2.53 (s, 3H, C2I—C$\underline{H}_3$), 3.86 (s, 3H, N1—C$\underline{H}_3$), 3.97 (m, 2H, N$_3$—C$\underline{H}_2$), 7.34 (s, 1H, C5I—$\underline{H}$), 7.45 (s, 1H, C4I-$\underline{H}$). FT-IR (neat): 3328 m, 2980 s, 2850 s, 1652 s, 1436 s, 1290 m, 1135 m, 1016 m, 751 w, 601 w cm$^{-1}$. MS/AP$^+$: 153 [M$^+$].

Example 8 is shown diagrammatically as follows:

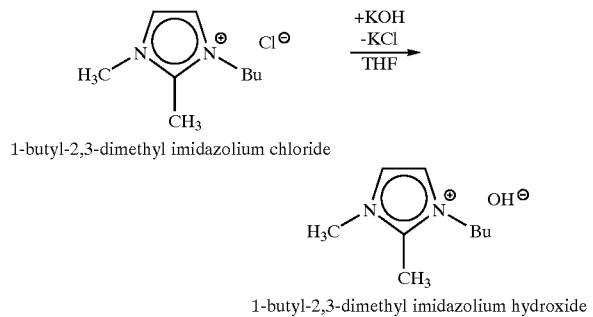

1-butyl-2,3-dimethyl imidazolium chloride 1-butyl-2,3-dimethyl imidazolium hydroxide

EXAMPLE 9

To demonstrate the recyclability of the ionic liquid medium, the basic ionic phase [bmin]BF$_4$ was investigated for the cross-aldol condensation reaction (Aldol II). After the conclusion of the reaction, the products are separated by vacuum distillation. The resulting ionic liquid phase was freed from organic sodium salts and reused as solvent medium for additional aldol reactions. Due to the formation of sodium-containing side products, it is necessary to adjust the sodium hydroxide concentration of the ionic liquid phase accordingly. The catalyst evaluation of the recycle study is shown in Table 5, which shows that the four reaction runs exhibited more than 99% conversion under the reaction conditions applied.

TABLE 5

Recycle study of the cross aldol reaction of propanal and 2-methyl-pentanal to 2,4-dimethyl-2-heptenal using the ionic liquid medium [bmin] BF$_4$ as a solvent and sodium hydroxide as catalyst.

| Reaction Run | Time (min.) | Temp. (° C.) | Conversion (wt %) |
| --- | --- | --- | --- |
| 1 | 180 | 95 | 100 |
| 2 | 180 | 96 | 99.8 |
| 3 | 180 | 99 | 99.9 |
| 4 | 180 | 97 | 99.7 |

The invention having been thus described, it will be obvious that the same may be varied in many ways without departing from the spirit and scope of the invention as defined by the following claims.

What is claimed is:

1. A method for forming aldol condensation products, comprising the step of reacting at least one aldehyde starting material in the presence of an ionic liquid medium and a basic catalyst at a temperature range of from about −20° C. to about 300° C. and at a pressure range of from about 1 atm to about 1000 atm for a sufficient time to form the aldol condensation products.

2. The method of claim 1 wherein the ionic liquid medium comprises a neutral ionic liquid medium having a cationic species and an anionic species.

3. The method of claim 2 wherein the cationic species of the neutral ionic liquid medium is selected from the group consisting of a pyridinium species and an imidazolium species, and derivatives thereof.

4. The method of claim 3 wherein the cationic species of the neutral ionic liquid medium is selected from the group consisting of 1-butyl-3-methyl imidazolium, 1-butyl-2,3-dimethyl imidazolium and 1-butyl-pyridinium.

5. The method of claim 2 wherein the anionic species of the neutral ionic liquid medium is selected from the group consisting of BF$_4^-$ and PF$_6^-$.

6. The method of claim 1 wherein the basic catalyst comprises a cationic species and an anionic species.

7. The method of claim 6 wherein the anionic species of the basic catalyst comprises an OH$^-$ species.

8. The method of claim 6 wherein the cationic species of the basic catalyst is selected from the group consisting of an alkali metal species and an alkali earth metal species.

9. The method of claim 8 wherein the cationic species of the basic catalyst is selected from the group consisting of a Na$^+$ species and a K$^+$ species.

10. The method of claim 1 wherein the temperature range comprises from about 80° C. to about 90° C.

11. The method of claim 1 wherein the sufficient time comprises about 3 hours.

12. The method of claim 1 further comprising the steps of:
   (a) separating the condensation products from the basic catalyst and the ionic liquid medium; and
   (b) recovering the ionic liquid medium and the basic catalyst.

13. The method of claim 12 further comprising the step of recycling the ionic liquid medium for forming additional aldol condensation products.

14. The method of claim 1 wherein the aldehyde starting material is selected from the group consisting of formaldehyde, acetaldehyde, propionaldehyde, n-butyraldehyde and isobutyraldehyde.

15. The method of claim 1 wherein two different aldehyde starting materials are reacted, one of which comprises formaldehyde.

16. The method of claim 15 wherein a second aldehyde starting material is selected from the group consisting of acetaldehyde, propionaldehyde, n-butyraldehyde and isobutyraldehyde.

17. A method for forming aldol condensation products, comprising the step of reacting at least one aldehyde starting material in the presence of a basic ionic liquid medium at a temperature range of from about −20° C. to about 300° C. and at a pressure range of from about 1 atm to about 1000 atm for a sufficient time to form the aldol condensation products.

18. The method of claim 17 wherein the basic ionic liquid medium comprises a cationic species and an anionic species.

19. The method of claim 18 wherein the anionic species of the basic ionic liquid medium comprises an OH⁻ species.

20. The method of claim 19 wherein the cationic species of the basic ionic liquid medium is selected from the group consisting of a pyridinium species and an imidazolium species, and derivatives thereof.

21. The method of claim 20 wherein the cationic species of the basic ionic liquid medium is selected from the group consisting of 1-butyl-3-methyl imidazolium, 1-butyl-2,3-dimethyl imidazolium and 1-butyl-pyridinium.

22. The method of claim 17 wherein the temperature range comprises from about 80° C. to about 90° C.

23. The method of claim 17 wherein the sufficient time comprises about 3 hours.

24. The method of claim 17 further comprising the steps of:

(a) separating the condensation products from the basic ionic liquid medium; and (b) recovering the basic ionic liquid medium.

25. The method of claim 24 further comprising the step of recycling the basic ionic liquid medium for forming additional aldol condensation products.

26. The method of claim 17 wherein the aldehyde starting material is selected from the group consisting of formaldehyde, acetaldehyde, propionaldehyde, n-butyraldehyde and isobutyraldehyde.

27. The method of claim 17 wherein two different aldehyde starting materials are reacted, one of which comprises formaldehyde.

28. The method of claim 27 wherein a second aldehyde starting material is selected from the group consisting of acetaldehyde, propionaldehyde, n-butyraldehyde and isobutyraldehyde.

29. The method of claim 1 or 17 wherein the aldehyde starting material comprise one or more aldehydes having the formula:

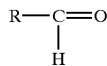

wherein

R=a hydrogen atom or a straight-chain, branched or cyclic aliphatic group having from 1 to 10 carbon atoms.

30. The method of claim 29 wherein R comprises a hydrogen atom or a straight-chain, branched or cyclic aliphatic group having from 1 to 6 carbon atoms.

31. The method of claim 30 wherein R comprises a hydrogen atom or a straight-chain, branched or cyclic aliphatic group having from 1 to 4 carbon atoms.

* * * * *